(12) United States Patent
Goodman et al.

(10) Patent No.: US 6,197,280 B1
(45) Date of Patent: Mar. 6, 2001

(54) PHARMACEUTICAL COMPOSITIONS AND DEVICES FOR THEIR ADMINISTRATION

(75) Inventors: Michael Goodman, Ampthill; David John Howlett, Grimston, both of (GB)

(73) Assignee: Bioglan Laboratories Limited, Hertfordshire (GB)

( * ) Notice: Subject to any disclaimer, the term of this patent is extended or adjusted under 35 U.S.C. 154(b) by 0 days.

(21) Appl. No.: 09/351,696

(22) Filed: Jul. 13, 1999

Related U.S. Application Data

(63) Continuation-in-part of application No. 08/913,226, filed on Sep. 9, 1997, now abandoned.

(51) Int. Cl.[7] ........................................ A61L 9/04
(52) U.S. Cl. ................................... 424/45; 424/43
(58) Field of Search ...................................... 424/45

(56) References Cited

U.S. PATENT DOCUMENTS

| | | | |
|---|---|---|---|
| 3,608,781 | 9/1971 | Flynn | 222/94 |
| 5,186,925 | 2/1993 | Cholcha | 424/43 |
| 5,190,029 | 3/1993 | Byron et al. | 128/200.14 |
| 5,474,758 | * 12/1995 | Kwon | 424/45 |
| 5,508,023 | * 4/1996 | Byron et al. | 424/45 |
| 5,607,662 | 3/1997 | Baskeyfield et al. | 424/46 |
| 5,653,961 | 8/1997 | McNally et al. | 424/45 |
| 5,674,473 | * 10/1997 | Purewal et al. | 424/45 |
| 5,775,321 | * 7/1998 | Alband | 128/200.23 |
| 5,776,432 | * 7/1998 | Schultz et al. | 424/45 |
| 5,980,867 | * 11/1999 | Tzou et al. | 424/45 |

FOREIGN PATENT DOCUMENTS

| | | |
|---|---|---|
| 970027 | 5/1963 | (GB) . |
| WO 92/14444 | 9/1992 | (WO) ............... A61K/9/12 |

* cited by examiner

Primary Examiner—Thurman K. Page
Assistant Examiner—P. E. McQueeney
(74) Attorney, Agent, or Firm—Wolf, Greenfield & Sacks, P.C.

(57) ABSTRACT

A device for providing pharmaceutical doses comprising a container, filed with a pharmaceutical composition including glyceryl trinitrate and 1,1,1,2-tetrafluoroethane, or 1,1,1,2,3,3,3-heptafluoropropane, as a propellant, and a valve arranged for delivering aerosol doses of said pharmaceutical composition to the exterior of the container, wherein at least a portion of the device is formed from a polyester.

27 Claims, 1 Drawing Sheet

PHARMACEUTICAL COMPOSITIONS AND DEVICES FOR THEIR ADMINISTRATION

This application is a Continuation-in-part (CIP) of prior application Ser. No. 08/913,226, filed Sep. 9, 1997, now abandoned.

BACKGROUND OF THE INVENTION

The present invention relates to a pharmaceutical composition comprising glyceryl trinitrate for delivery in aerosol form and to a device for delivering such a composition as an aerosol.

Glyceryl trinitrate is well established in the treatment and prophylaxis of angina pectoris and, when used to relieve acute attacks, is most commonly administered lingually, sub-lingually or buccally in the form of a spray, buccal tablet or chewable lozenge. Absorption of glyceryl trinitrate via the oral mucosa, particularly the sub-lingual oral mucosa, is rapid and haemodynamic effects and relief from pain are almost immediate.

Current aerosol spray formulations of glyceryl trinitrate use one or more chlorofluorocarbon as a propellant; dichlorodifluoromethane being commonly used. However, chlorofluorocarbons have been implicated in the depletion of the ozone layer and their production, therefore, is being phased out. It as been found that certain hydrofluorocarbons, which are both of low toxicity and of suitable vapour pressure for use as aerosol propellants, are significantly less harmful to the ozone layer. Among such hydrofluorocarbons, 1,1,1,2-tetrafluoroethane (HFC-134a) and 1,1,1,2,3,3,3-heptafluoropropane (HFC-227) have been proposed as suitable propellants for pharmaceutical aerosols.

It has now been found that HFC-134a and HFC-227 can be used in combination with glyceryl trinitrate, without causing any degradation of the latter or reduction in its physiological effect.

Devices for administering metered aerosol doses of pharmaceutical preparations are well known in the art. Such devices include those disclosed in WO 92/11190, U.S. Pat. No. 4,819,834, U.S. Pat. No. 4,407,481. Many of these devices include metering valves having components formed from plastic materials, such as the valves available from Bespak PLC of Bergen Way, Kings Lynn, Norfolk PE30 2JJ, United Kingdom, in which the valve core, metering chamber and some other structural components are formed from plastic materials. The plastic materials currently used for forming these structural parts in valves employed with chlorofluorocarbon containing formulations of glyceryl trinitrate include certain acetal co-polymers.

Although the plastics employed to manufacture metering valves, including the aforementioned acetal co-polymers, have also been found to be stable in the presence of HFC-134a alone, the applicants, to their surprise, have determined that many of these plastics materials can be caused to swell in the presence of formulations which include glyceryl trinitrate and HFC-134a. When such swelling takes place in a valve, the fit of mutually slidable components, such as metering chambers and valve cores, is adversely effected and they can bind together or become loose, causing the valve to leak or cease functioning altogether.

SUMMARY OF THE INVENTION

This problem was solved in accordance with a first aspect of the invention which provides a device for providing pharmaceutical doses, comprising a container, filled with a pharmaceutical composition including glyceryl trinitrate and 1,1,1,2-tetrafluoroethane (HFC-134a) or 1,1,1,2,3,3,3-heptafluoropropane (HFC-227) as a propellant, and valve means arranged for delivering aerosol doses of said pharmaceutical composition to the exterior of the container, wherein at least a portion of the device is formed from a polyester. Preferably, the valve means includes at least one component formed from a polyester which component, more preferably, is a metering chamber and/or a valve core. Preferably, devices in accordance with the invention are arranged to provide metered doses of glyceryl trinitrate.

In further embodiments, the container comprises a polyester and, preferably, consists of metal lined with a polyester. The canister cap can also be so formed.

Apart from allowing the aforementioned swelling problem to be avoided, an advantage of the present invention is that use of expensive metal valve components can be avoided.

During the course of the work leading to the present invention, tests carried out on glyceryl trinitrate/ethanol/HFC-134a filled metered dose aerosol devices, with acetyl copolymer or nylon valve components, showed that they failed to provide uniform doses after storage under controlled conditions. Such effects are normally associated with problems involving the gaskets or seals employed within the valve mechanisms. Thus, it came as a surprise to the applicants when they discovered that these failures were being caused by the valve components swelling to an unacceptable extent, particularly since at least one of the materials used to form them (acetyl co-polymer) was known to be stable in the presence of HFC-134a, either alone or in admixture with ethanol, or conventional glyceryl trinitrate/ethanol/chlorofluoro carbon formulations.

The preferred polyesters are polyalkylene benzene dicarboxylates, more preferably polyalkylene terephthalates and, most preferably, a polybutylene terephthalate.

Such materials, preferably, have a density of about 1.3g/cm$^3$ and a water absorption of about 0.6% (23° C. saturation). The polyesters, also, are preferably partially crystalline in nature and have a crystalline melting range of 220–225° C.

Examples of suitable polybutylene terephthalates include those available under the Trademark Celanex® from Hoechst UK Limited, Walton Manner, Milton Keynes, Bucks MK7 7AJ, United Kingdom. Particularly preferred are Celanex® 2500 and Celanex® X 500/2.

The preferred propellant for use in the inventive device is HFC-134a and, in embodiments, the preparation further comprises, as a co-solvent, a lower alkyl alcohol, preferably ethanol, or a pharmaceutically acceptable polyol, preferably propylene glycol, glycerol or polyethylene glycol. The preferred co-solvent is ethanol. The lower alkyl alcohols can be $C_2$–$C_4$ alkyl alcohols.

In embodiments, the composition included in the inventive device further comprises a flavouring oil, preferably peppermint oil Ph Eur. In all embodiments, it is preferred that the composition within the device comprises a solution of the propellant, glyceryl trinitrate and any co-solvent and flavouring agent employed.

In a second aspect, the invention provides a pharmaceutical composition for use in a device in accordance with the first aspect of the invention, comprising glyceryl trinitrate and HFC-134a or HFC-227 as a propellant. The preferred propellant is HFC-134a and it is further preferred that ethanol is included in the preparation.

In preferred embodiments of the invention, pharmaceutical compositions for use in devices in accordance with the first, aspect of the invention can comprise 75–95% w/w HFC-134a, or HFC-227 as a propellant, an optional amount of 0.5–2% w/w of a flavouring oil, and 5–25% w/w of a combination of 2–8% w/w glyceryl trinitrate and 92–98% w/w of a lower alkyl alcohol or a pharmaceutically acceptable polyol as a co-solvent. An advantage of such embodiments is that, because they include a greater proportion of volatile propellant than usual, the risk of a potentially clogging deposit of non-volatile material building up around the outlet nozzel of the device is minimised. This is particularly so in embodiments where no non-volatile agents, other than the active agent and a minimal amount (as specified above) of flavouring oil, are included in the composition.

Preferably, the flavouring oil is peppermint oil. The preferred lower alcohol is ethanol and the preferred pharmaceutically acceptable polyols are propylene glycol, glycerol and polyethylene glycol. It is preferred that compositions in accordance with the second aspect of the invention are in the form of liquid solutions, when maintained under pressure in devices in accordance with the first aspect of the invention, and are especially suited to use therein, since they do not cause significant degradation of the valve components employed in such devices.

Further excipients can be included in the formulations employed in the present invention. For example, neutral oils and surfactants (the latter for aiding the smooth operation of the valve), as are well known to those skilled in the art, may be included.

In a third aspect, the invention provides the use of a polyester in contact with a composition comprising glyceryl trinitrate, HFC-134a and/or HFC-227. Preferably the composition is in accordance with the second aspect of the invention, the polyester is one of those described above, and the use takes place in a metered dose dispensing aerosol device.

An embodiment of the first aspect of the present invention will now be described, by way of example only, and with reference to the following drawing.

DETAILED DESCRIPTION OF THE INVENTION

Figure 1:
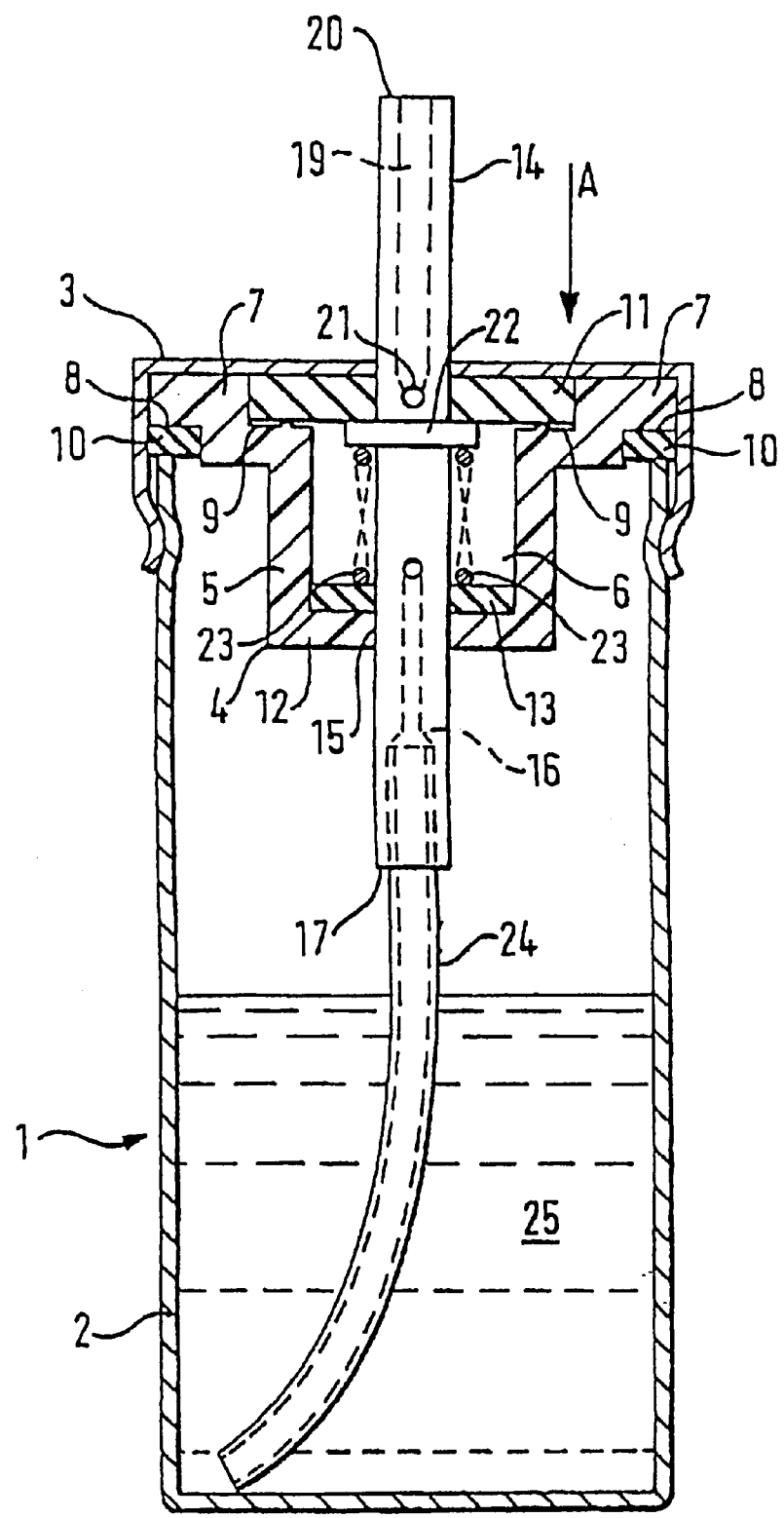
FIG. 1 is a cross sectional view of an embodiment of a device in accordance with the invention.

The device 1 comprises a substantially cylindrical canister 2 sealed with a cap 3. Both the canister 2 and the cap 3 are formed from an aluminium alloy and can be lined with a polyester (such as Celanex® 2500) or a lacquer (not shown).

A valve body moulding 4 comprises a cylindrical portion 5, which defines a metering chamber 6 and a stepped flange portion 7, and is formed by injection moulding from Celanex® 2500. The stepped flange portion 7 defines a first and outwardly facing annular seat 8 and a second, inwardly facing annular seat 9. The first annular seat 8 accommodates an annular sealing ring 10 and the second annular seat 9 accommodates a first sealing washer 11. The first sealing washer 11 is located so as to cooperate with the cylindrical portion 5 of the valve body moulding 4, in defining the metering chamber.6.

A base 12 of the cylindrical portion 5 of the valve body moulding 4 completes the boundary to the metering chamber 6 and provides a seat for a second sealing washer 13.

The sealing ring 10 and the first and second sealing washers 11 and 13 can be formed from a butyl rubber, neoprene or one of the elastomers disclosed for such purposes in WO 92/11190.

An elongate, substantially cylindrical and partially hollow valve core 14 is slidably located within the first and second sealing washers 11 and 13 and extends through an orifice is, defined in the base 12. The valve core 14 is formed by injection moulding from Celanex® 2500.

A stepped inlet passage 16 communicates between a first end 17 of the valve core 14 and an inlet orifice 18, formed through the side of the valve core 14. In a likewise manner, an outlet passage 19 communicates between the second end 20 of the valve core 14 and an outlet orifice 21 formed through the side of the valve core 14. An annular flange 22 extends radially outwardly from the valve core 14 between the inlet and outlet orifices 18 and 21 and adjacent to the outlet orifice 21.

A stainless steel compression coil spring 23 acts between the annular flange 22 and the second sealing washer 13, urging the annular flange 22 into contact with the first sealing washer 11, such that the outlet orifice 21 lies inside the first sealing washer 11 and is thereby isolated from the metering chamber 6. In this position, as shown in FIG. 1, the inlet orifice 18 is located within the metering chamber 6. A flexible tube 24 is engaged within the stepped inlet passage 16 and extends from the valve core 14 to the base of the canister 2 (as shown in FIG. 1). Thus, the inlet orifice 18 is in communication with a region within the canister 2 adjacent to its base 12.

The cap 3 is firmly attached to the canister 2 by crimping and, thus, holds the assembly of the valve body moulding 4, valve core 14, coil spring 23, sealing washers 11 and 13 and sealing ring 10 in place as shown in FIG. 1, with the sealing ring 10 and first sealing washer 11 sufficiently compressed to seal the interior of the device 1 and prevent the egress of its contents.

Downward movement of the valve core, in the direction of arrow A, against the action of the spring 22 will bring the outlet orifice 21 into the metering chamber immediately after the first orifice 18 has been sealed from the metering chamber 6 by the second sealing washer 13.

When filled with a composition in accordance with the present invention, as shown at 25, the device 1 will provide metered doses of the composition when used as follows. The device 1 should be held in the position shown in FIG. 1, so that the composition 25, by virtue of its pressure, enters the metering chamber 6 via the tube 24, the inlet passage 16 and the inlet orifice 18. Subsequent depression of the valve core 14, in the direction of arrow A, seals the inlet orifice 18 and hence the remainder of the canister 2, from the metering chamber 6 and opens the outlet passage to the metering chamber 6, via the outlet orifice 21. Since the composition 25 in the metering chamber 6 is pressurised with the propellant, it will be expelled from the metering chamber 6 through the outlet orifice 21 and the outlet passage 19. If the valve core 14 is then allowed to return to the position shown in FIG. 1, under the influence of the spring 22, the outlet orifice 21 is again sealed from the metering chamber 6 and the metering chamber 6 will be filled with pressurised composition 25 from the canister 2, via the tube 21, stepped inlet passage 16 and inlet orifice 18.

EXAMPLE 1

A composition of glyceryl trinitrate with HFC-134a suitable for use in a device as described above is formulated from the following ingredients:

| Component | Mg/dose | percent w/w | g/can |
|---|---|---|---|
| Glyceryl trinitrate | 0.4 | 0.7 | 0.099 |
| Ethanol 96% BP | 7.6 | 13.2 | 1.866 |
| Peppermint oil Ph Eur | 0.8 | 1.4 | 0.205 |
| HFC-134a | 48.2 | 84.7 | 12.02 |
| Total | 57.00 | 100 | 14.19 |

The ethanol and glyceryl trinitrate is obtained as a 5% glyceryl trinitrate solution in 96% ethanol BP from commercial sources. The peppermint oil is added to the glyceryl trinitrate/ethanol solution and mixed thoroughly. 2.17 g of the resulting solution is then placed in the canister 2 and the valve assembly, comprising the valve body moulding 4, first sealing washer 11, second sealing washer 13, spring 22, tube 23, and annular seal 10 are then sealed onto the canister 2 by crimping as shown in FIG. 1 by the cap 3. The propellant (HFC-134a) is then added to the canister, by being forced through the valve core 14 at great pressure, and the complete device is then checked for leaks. After the propellant has entered the canister it dissolves with the remaining portions of the composition.

In a preferred embodiment, the weight of each expelled dose of the above formulation is between 51 and 63 milligrams, providing 0.4 milligrams of glyceryl trinitrate per dose. This embodiment should provide a minimum of 200 doses.

What is claimed is:

1. A device for providing pharmaceutical doses, comprising a container, filled with a pharmaceutical composition including glyceryl trinitrate and 1,1,1,2-tetrafluoroethane (HFC-134a) or 1,1,1,2,3,3,3-heptafluoropropane (HFC-227) as a propellant, and a valve arranged for delivering aerosol doses of said pharmaceutical composition to the exterior of the container, wherein at least a portion of the device is formed from a polyester.

2. A device as claimed in claim 1, wherein the propellant is HFC-134a.

3. A device as claimed in claim 1, wherein the preparation further comprises a lower alkyl alcohol, or a pharmaceutically acceptable polyol.

4. A device as claimed in claim 1, wherein the preparation further comprises a flavouring oil.

5. A device as claimed in claim 1, wherein the pharmaceutical composition comprises 75–95% w/w propellant, 5–25% w/w of a combination of 2–8% w/w glyceryl trinitrate and 92–98% w/w of a lower alkyl alcohol or a pharmaceutically acceptable polyol, and optionally a flavoring oil present in an amount of 0.5–2% w/w.

6. A device as claimed in claim 3 or claim 5, wherein the lower alkyl alcohol is ethanol.

7. A device as claimed in claim 3 or claim 5, wherein the polyol is propylene glycol, glycerol or polyethylene glycol.

8. A device as claimed in claim 4, wherein the flavouring oil is peppermint oil Ph Eur.

9. A device as claimed in claim 1, wherein the valve includes at least one component formed from a polyester.

10. A device as claimed in claim 9, wherein two relatively movable valve components are formed from a polyester.

11. A device as claimed in claim 10, wherein said relatively movable valve components are mutually slidable.

12. A device as claimed in claim 9, wherein said component is a metering chamber.

13. A device as claimed in claim 9, wherein said component is a valve core.

14. A device as claimed in claim 1, wherein the container includes a canister body comprising a polyester.

15. A device as claimed in claim 14, wherein the canister body is formed from metal lined with the polyester.

16. A device as claimed in claim 1, wherein said portion is a canister cap or lining.

17. A device as claimed in any of claims 1, 9, 10, 11, 12, 13, 14, 15 or 16, wherein the polyester is a polyalkylene benzene dicarboxylate.

18. A device as claimed in claim 17, wherein the polyester is a polyalkylene terephthalate.

19. A device as claimed in claim 18, wherein the polyester is a polybutylene terephthalate.

20. A device as claimed in claim 3 or claim 5 wherein the composition comprises ethanol.

21. A device as claimed in claim 1, for use in treating angina pectoris.

22. A container formed at least in part from a polyester, wherein said polyester is in contact with a composition comprising glyceryl trinitrate, HFC-134a and/or HFC-227.

23. A container as claimed in claim 22, wherein the polyester is as defined in claim 17.

24. A container as claimed in claim 22, wherein said polyester is in contact with a pharmaceutical composition comprising 75–95% w/w 1,1,1,2-tetrafluoroethane (HFC-134a) or 1,1,1,2,3,3,3-heptafluoropropane (HFC-227) as a propellant, an optional amount of 0.5–2% w/w of a flavouring oil, and 5–25% w/w of a combination of 2–8% w/w glyceryl trinitrate and 92–98% w/w of a lower alkyl alcohol or a pharmaceutically acceptable polyol and optionally a flavoring oil present in an amount of 0.5–2% w/w.

25. A container as claimed in claim 24, wherein the flavouring oil is peppermint oil.

26. A container as claimed in claim 24, wherein the lower alcohol is ethanol.

27. A container as claimed in claim 24, wherein the pharmaceutically acceptable polyol is propylene glycol, glycerol or polyethylene glycol.

* * * * *